(12) United States Patent
Yock et al.

(10) Patent No.: US 11,738,212 B2
(45) Date of Patent: Aug. 29, 2023

(54) RIGID PHANTOM FOR END-TO-END VERIFICATION OF ADAPTIVE RADIOTHERAPY SYSTEMS

(71) Applicant: Vanderbilt University, Nashville, TN (US)

(72) Inventors: Adam D. Yock, Nashville, TN (US); Abby E. Dare, Nashville, TN (US); Michael Price, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 17/336,862

(22) Filed: Jun. 2, 2021

(65) Prior Publication Data

US 2021/0370100 A1  Dec. 2, 2021

Related U.S. Application Data

(60) Provisional application No. 63/033,435, filed on Jun. 2, 2020.

(51) Int. Cl.
   *A61N 5/10*    (2006.01)
(52) U.S. Cl.
   CPC .......... *A61N 5/1075* (2013.01); *A61N 5/1039* (2013.01); *A61N 2005/1076* (2013.01)
(58) Field of Classification Search
   CPC .............. A61N 5/1039; A61N 5/1075; A61N 2005/1076
   See application file for complete search history.

(56) References Cited

U.S. PATENT DOCUMENTS

| 6,231,231 B1* | 5/2001 | Farrokhnia | A61B 6/583 378/207 |
| 8,173,968 B1* | 5/2012 | Nelms | A61N 5/1071 250/370.07 |
| 2004/0120560 A1* | 6/2004 | Robar | A61N 5/1048 382/128 |
| 2004/0228435 A1* | 11/2004 | Russell | A61N 5/1048 378/18 |
| 2005/0151071 A1* | 7/2005 | Nilsson | A61N 5/1048 250/252.1 |
| 2008/0240364 A1* | 10/2008 | Main | A61N 5/1048 250/252.1 |
| 2008/0298540 A1* | 12/2008 | Serban | A61N 5/1048 378/18 |
| 2010/0288916 A1* | 11/2010 | Cho | A61N 5/1071 378/207 |
| 2011/0166410 A1* | 7/2011 | Gutierrez | A61N 5/1015 600/3 |

(Continued)

*Primary Examiner* — Blake C Riddick
(74) *Attorney, Agent, or Firm* — TAROLLI, SUNDHEIM, COVELL & TUMMINO L.L.P.

(57) ABSTRACT

Systems and methods associated with a phantom assembly are provided. A housing includes a plurality of slots and is formed from a first material having a first appearance under a selected imaging modality. A plurality of inserts are each configured to be received by one of the plurality of slots. At least one insert includes a target formed from a second material having a second appearance under the selected imaging modality, such that the target is readily distinguishable from the housing under the selected imaging modality. The target includes a hollow portion that can be accessed via a removable plug.

12 Claims, 3 Drawing Sheets

(56) References Cited

U.S. PATENT DOCUMENTS

| | | | |
|---|---|---|---|
| 2015/0085993 A1* | 3/2015 | Scheib | A61N 5/1071 378/207 |
| 2015/0316657 A1* | 11/2015 | Ruschin | G01T 1/04 250/252.1 |
| 2016/0256711 A1* | 9/2016 | Pappas | A61N 5/1075 |
| 2017/0080254 A1* | 3/2017 | Scheib | A61N 5/1049 |
| 2019/0060673 A1* | 2/2019 | McKenna | G01T 1/02 |
| 2019/0175951 A1* | 6/2019 | Yu | A61B 6/032 |
| 2019/0329072 A1* | 10/2019 | Magro | G01T 1/161 |
| 2020/0232938 A1* | 7/2020 | Fitzgerald | G06T 7/0004 |
| 2021/0145395 A1* | 5/2021 | Boone | A61B 6/4085 |
| 2022/0139262 A1* | 5/2022 | Singhrao | G01R 33/58 378/207 |

* cited by examiner

|     | 224   | 225   | 226   | 227   |
| --- | ----- | ----- | ----- | ----- |
| 224 | 95%   | 90.8% | 81.9% | 82.6% |
|     | 0.96  | 1.47  | 0.98  | 1.56  |
| 225 | 59.3% | 95%   | 54.9% | 79.5% |
|     | 0.65  | 0.97  | 0.65  | 1.03  |
| 226 | 83%   | 85.2% | 95%   | 88.3% |
|     | 0.99  | 1.48  | 0.98  | 1.57  |
| 227 | 50.5% | 79.5% | 54.8% | 95%   |
|     | 0.63  | 0.94  | 0.62  | 0.99  |

FIG. 3

RIGID PHANTOM FOR END-TO-END VERIFICATION OF ADAPTIVE RADIOTHERAPY SYSTEMS

RELATED APPLICATIONS

This application claims priority to U.S. Provisional Patent Application Ser. No. 63/033,435, filed Jun. 2, 2020 and entitled "RIGID PHANTOM FOR END-TO-END VERIFICATION OF ADAPTIVE RADIOTHERAPY SYSTEMS," which is hereby incorporated by reference in its entirety.

TECHNICAL FIELD

This disclosure relates to medical treatment systems and is specifically directed to a rigid phantom for end-to-end verification of adaptive radiotherapy systems.

BACKGROUND

Online adaptive radiotherapy is an emerging technique that features the ability to rapidly re-plan the treatment at each session. Because the steps required in re-planning are both time-intensive and computationally-intensive, systems have been developed to make this technique technologically feasible. To verify the performance of these systems, users must conduct a battery of tests including a comprehensive end-to-end test of the entire process.

SUMMARY

In one example, an assembly includes a housing that includes a plurality of slots and is formed from a first material having a first appearance under a selected imaging modality. A plurality of inserts are each configured to be received by one of the plurality of slots. At least one insert includes a target formed from a second material having a second appearance under the selected imaging modality, such that the target is readily distinguishable from the housing under the selected imaging modality. The target includes a hollow portion that can be accessed via a removable plug.

In another example, a method is provided. A first target on a phantom is imaged to provide a first image. A first radiotherapy treatment plan is created for an adaptive radiotherapy system from the first image. All or a portion of the phantom is rotated to align a second target on the phantom with the adaptive radiotherapy system. The second target on the phantom is imaged to provide a second image. A second radiotherapy treatment plan is created for the adaptive radiotherapy system from the second image. An expected dose for a selected one of the first radiotherapy treatment plan and the second radiotherapy treatment plan when applied to the second target is determined. The selected radiotherapy treatment plan is applied to the second target on the phantom to provide a dosage measurement at a dosimeter associated with the phantom. A performance of the adaptive radiotherapy system is evaluated according to the expected dose and the dosage measurement to provide a metric representing the performance of the radiotherapy system.

In a further example, an assembly includes a housing that includes a plurality of slots and is formed from a first material having a first appearance under a selected imaging modality. A plurality of inserts are each configured to be received by one of the plurality of slots. Each insert includes a frame, formed from one of the first material and a second material having the first appearance under the selected imaging modality, and a target, formed from a third material having a second appearance under the selected imaging modality, such that the target is readily distinguishable from the housing and the frame under the selected imaging modality. A first target of the plurality of targets has a known geometric relationship to a second target of the plurality of targets and a hollow portion that can be accessed via a removable plug.

BRIEF DESCRIPTION OF THE DRAWINGS

FIG. 3 is a chart illustrating the coverage percentage and conformity index for plans generated on one target of the targets from one implementation of the rigid phantom assembly of FIG. 2.

DETAILED DESCRIPTION

Figure 1:
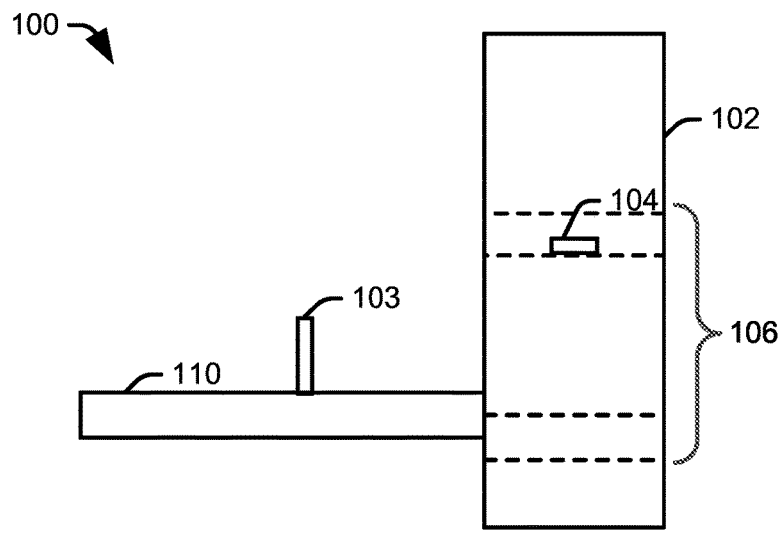
FIG. 1 is a side view of an imaging device and a rigid phantom assembly.

This disclosure relates to systems and methods for verifying an adaptive radiotherapy system using a rigid phantom. The phantom features multiple objects that can be used as radiotherapy treatment targets. It will be appreciated that the verification process can test all the faculties and processes of the adaptive radiotherapy system including image acquisition and registration, structure re-contouring, plan reoptimization, dose calculation, plan quality assurance, and plan delivery independently, or in select or comprehensive combination. FIG. 1 illustrates a system 100 that includes a radiotherapy apparatus 102 and a phantom assembly 103. The radiotherapy apparatus includes a radiation source 104 which can provide radiation to a region of interest. In this example, the radiation source 104 is a radiotherapy treatment source for radiotherapy apparatus 100. The radiotherapy apparatus 102 also includes an imaging system 106, such as a computer tomography scanner, that can image subjects within the region of interest. It will be appreciated that the imaging system 106 can share components with the radiation source 104.

Generally, for radiotherapy treatment, the radiation source 104 emits a treatment beam, which is directed at and irradiates tissue of interest of a patient on a patient support 110, which is used to position a patient for treatment and imaging. The radiation source 104 can be rotated to one or more predetermined angular locations and/or the patient support 110 can be moved to facilitate directing the treatment beam according to a radiotherapy plan. As shown in FIG. 1, the phantom assembly 103 can be placed on the patient support 110 of the imaging device 106, and an image can be taken with the imaging device, allowing for the appearance of one or more targets on the phantom assembly 103. Since the size, shape, and orientation of the targets are known, the image captured at the imaging device 102 can be compared to an expected appearance of the target to evaluate the imaging device and the quality of images it produces. The rigid phantom assembly 103 can also be instrumented with various dosimeters and targeted with a treatment beam to measure the dose of ionizing radiation produced by the radiation source 104 at the target region of the phantom assembly.

In accordance with an aspect of the present invention, the phantom assembly 103 includes a housing with a plurality of slots. The housing is formed from a first material having a desired appearance when imaged by the imaging device 102. The slots can each receive an insert with a frame and a target, formed from another material, generally selected to mimic a type of tissue. The morphology of each target is precisely characterized and designed to have a known relationship to the morphology of the other targets, such as known differences in size, shape, or position, with the morphological relationships designed to mimic the ways in which a patient's anatomy can change throughout the course of treatment. The user can design a treatment plan based on one object, and attempt to deliver it to another object featuring different morphology. A digital representation of the phantom can also be used for in-silico tests.

Figure 2:
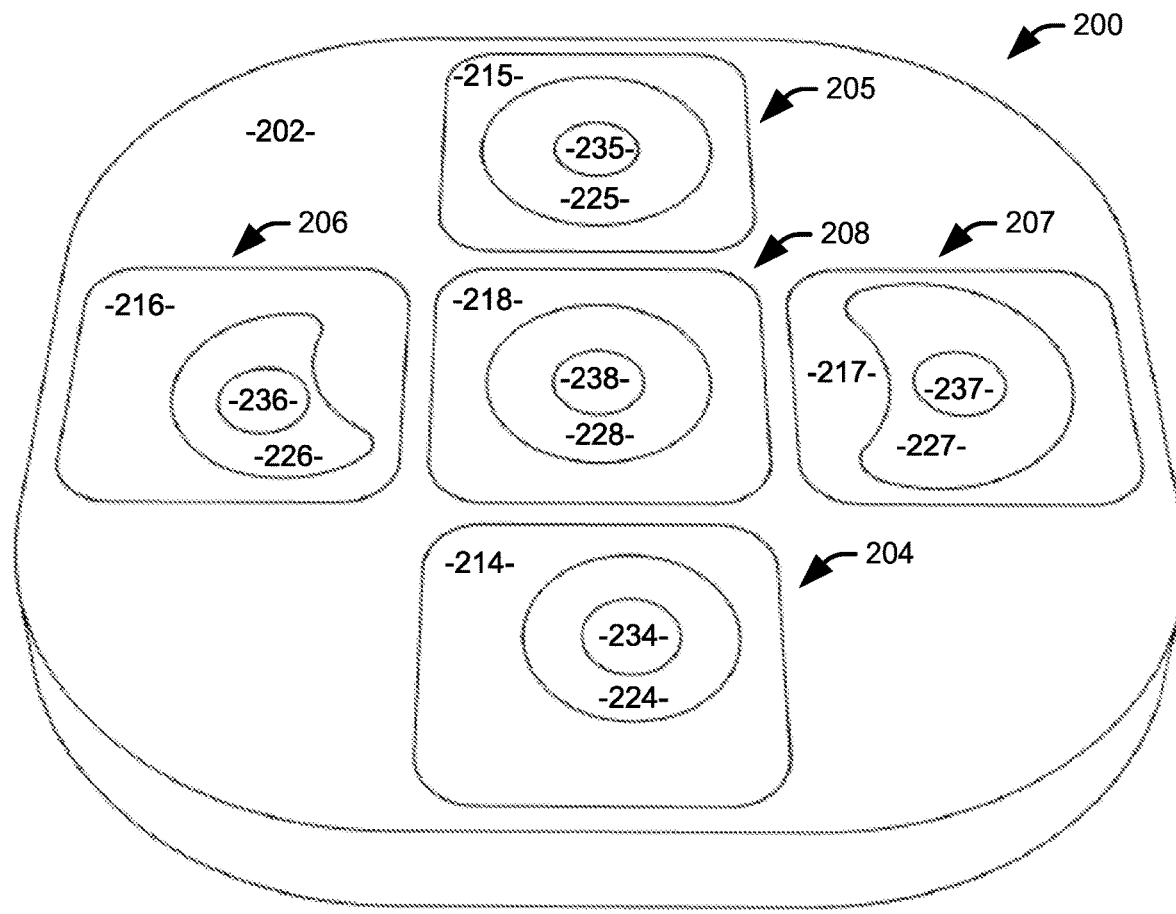
FIG. 2 depicts an example of rigid phantom assembly for use in an adaptive radiotherapy system.

FIG. 2 depicts one example of a rigid phantom assembly 200 for use in verifying an adaptive radiotherapy system. The assembly 200 includes a housing 202 having a plurality of slots, each configured to receive one of a plurality of inserts 204-208. The housing 202 can be formed from a material that has an appearance for a given imaging modality that is similar to water. For example, when the imaging modality is X-ray computed tomography, the material of the housing 202 can be selected to have a linear attenuation value similar to that of water, such as RMI-457 Solid Water®, Virtual Water®, and Plastic Water®. In one example, the housing is formed from a high-density polyethylene slab.

Each of the plurality of inserts 204-208 can include a frame 214-218, made from a material similar to the housing 202 enclosing a target 224-228 formed from a material that has an appearance for a given imaging modality that is similar to a target tissue type. It will be appreciated, however, that the housing 202 can be configured to receive the targets 224-228 directly, without the frames 214-218, although in this implementation, the targets 224-228 could not be readily rotated within the housing. In one example, the targets 224-228 are formed from an acrylic and are intended to mimic the appearance of soft tissue in a computed tomography image. It will be appreciated, however, that a target could be formed from a high-density plastic that is intended to mimic the appearance of bone in a computed tomography image. In one example, one or more targets can be made of different materials, which can mimic the appearance of one or more tissue types. In one example, the inserts 204-208 can be removed from the housing 202 and either replaced with another insert, either one of the depicted inserts 204-208 or another insert, (not shown) or rotated ninety, one hundred eighty, or two hundred seventy degrees. In another example, the inserts 204-208 can be octagonal to allow rotation to be performed in forty-five degree increments. In a further example, the inserts can be circular to allow for arbitrary rotation. It will be appreciated that various shapes, generally regular polygons to allow for various rotations of the inserts.

Each target 224-228 can include a hollow interior portion, accessible via one or more removable plugs 234-238 to allow for one or more dosimeters (e.g., thermoluminescent dosimeters (TLD), optically stimulated luminescent dosimeters (OSLD), ion chambers) to be inserted into the target area. In different implementations, the removable plugs and dosimeters could be located at various positions within each interior portion, including deliberately placed off-center to emphasize the varying shapes of targets. In some implementations, multiple dosimeters can be distributed through the targets, frames, or housing of the phantom. A set of phantom assemblies can be stacked to join the interior surfaces of the targets as to allow for a larger dosimeter to be placed within the stack of phantom assemblies. Alternatively or additionally, radiochromic films can be placed between phantom assemblies in a stack to measure a cross-sectional distribution of an applied dose of radiation. In practice, the phantom to be imaged by a given imaging system will have a desired thickness associated with the imaging modality. A phantom of the appropriate thickness can be formed from a single phantom assembly 200 or multiple, thinner phantom assemblies that are stacked to provide the desired thickness.

In one example, a set of the soft tissue targets 224-227 can be precisely designed to have a known geometric relationship relative to the other targets. The known geometric relationship between objects can be interpreted as the geometric transformation required to convert the morphology of one object to that of the other. The relationships can be selected to mimic changes in anatomy during radiotherapy. In the illustrated example, in the orientations in which the targets 224-227 are shown in FIG. 2, a first target 224 represents a second target 225 after a reduction in volume (e.g., by around a third), a known translation (e.g., seven millimeters), and an effective local rotation of twenty degrees. Similarly, a third target 226 represents a fourth target 227 after a thirty-six percent reduction in volume, a translation of seven millimeters, and an effective local rotation of twenty degrees. Each of the third target 226 and the fourth target 227 include a modification of the first target 224 and the second target 225, respectively, to include an asymmetric deformation.

From these known relationships, it is possible to generate an expected dose for each object given a radiotherapy plan designed for another object. FIG. 3 is a chart 300 illustrating the coverage percentage and conformity index for plans generated on one target of the targets 224-227 from the example assembly of FIG. 2 when delivered on another of the targets. Each column 302-305 of the chart represents a radiotherapy plan generated for one of targets 224-227, and each row 312-315 of the chart lists the values for the coverage percentage and conformity index of that plan for the target represented by that row, with the coverage percentage on the top and the conformity index on the bottom. It will be appreciated that these known relationships among the targets allow for simulation of the effects of changes in anatomy on dose calculations, allowing for appropriate evaluation of an adaptive radiotherapy system.

Changing test objects of different morphologies can be achieved multiple ways. Either a given insert 204-208 of the phantom 200, or the entire phantom, can be shifted, rotated, or exchanged such that the object used for the original treatment plan is replaced by another. It will be appreciated that rotating the housing 202 of the phantom replaces one test object, represented by a target 224-227, with another, allowing for evaluation of a DIR system with respect to changes in position, orientation, and shape depending on the geometric relationship of the two objects. Accordingly, the phantom can be imaged and irradiated while simulating changes in tissue morphology, allowing for its use as a ground truth to evaluate adaptive radiotherapy workflows and processes.

Figure 4:
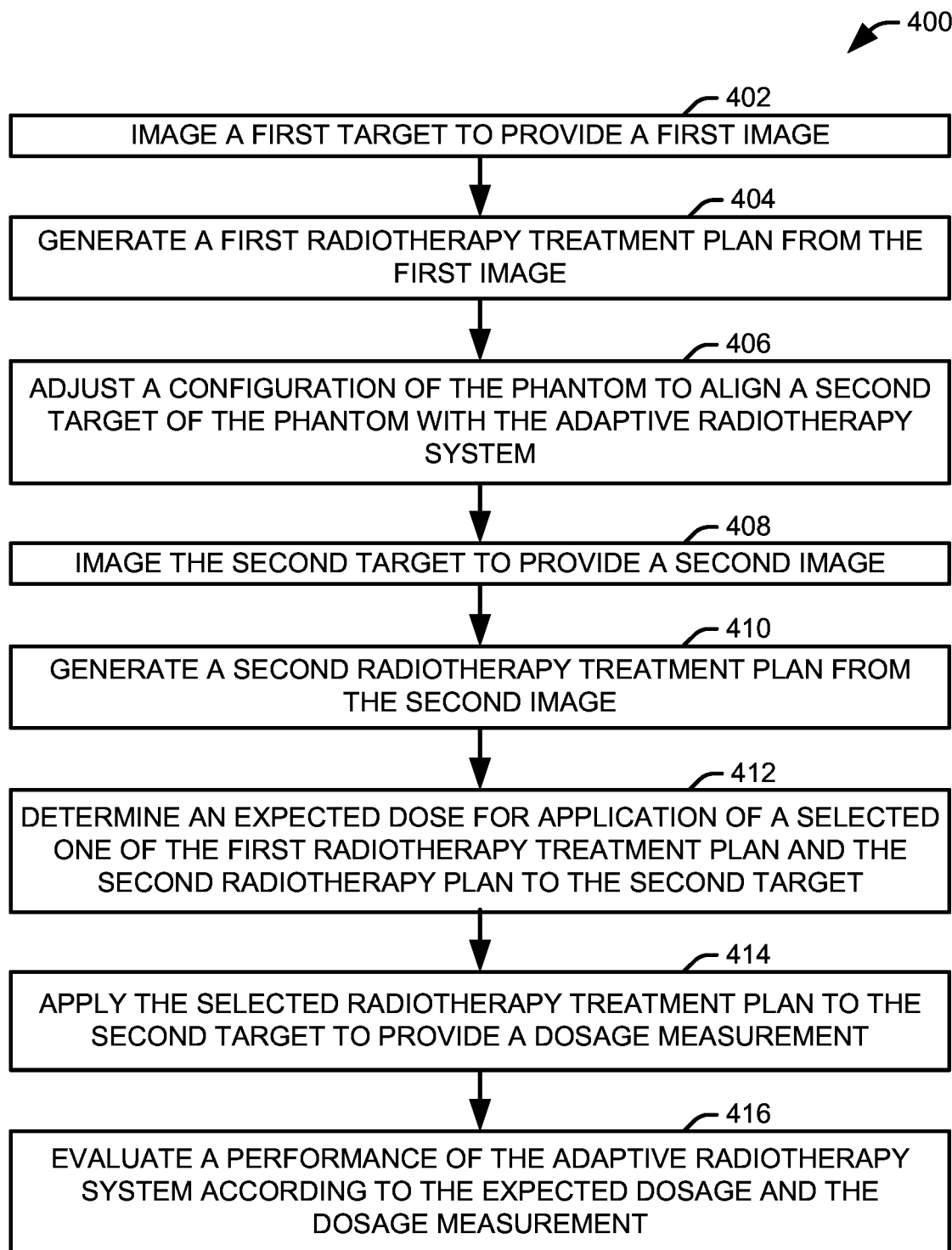
FIG. 4 depicts one method of evaluating an adaptive radiotherapy system using a rigid phantom.

In view of the foregoing structural and functional features described above in FIGS. 1-3, an example method will be better appreciated with reference to FIG. 4. While, for purposes of simplicity of explanation, the method of FIG. 4 is shown and described as executing serially, it is to be understood and appreciated that the present invention is not limited by the illustrated order, as some actions could in other examples occur in different orders and/or concurrently from that shown and described herein.

FIG. 4 illustrates one example of a method 400 for evaluating an adaptive radiotherapy system using a rigid phantom. At 402, a first target on a phantom is imaged to provide a first image. It will be appreciated that the first target can be imaged at an adaptive radiotherapy system or a separate imaging system, such as a computed tomography (CT) scanner or a magnetic resonance imaging (MRI) system. At 404, a first radiotherapy treatment plan is created for an adaptive radiotherapy system from the first image. It will be appreciated that the first radiotherapy treatment plan may be generated at a system other than the adaptive radiotherapy system. At 406, the configuration of the phantom is adjusted to align a second target on the phantom with the adaptive radiotherapy system. For example, all or a portion of the phantom can be rotated to align the second target with the adaptive radiotherapy system. Alternatively, the second target can be inserted into the phantom in place of the first target. At 408, the second target on the phantom is imaged to provide a second image.

At 410, a second radiotherapy treatment plan is created for the adaptive radiotherapy system from the second image. It will be appreciated that the first radiotherapy plan can be adapted based on the differences between the first and second images to more efficiently create the second radiotherapy plan at the adaptive radiotherapy system. At 412, an expected dose for a selected one of the first radiotherapy plan and the second radiotherapy treatment plan when applied to the second target is determined. At 414, the selected radiotherapy treatment plan is applied to the second target on the phantom to provide a dosage measurement at a dosimeter associated with the phantom. A performance of the adaptive radiotherapy system is evaluated according to the expected dose and the dosage measurement at 416 to provide a metric representing the performance of the radiotherapy system.

It will be appreciated that, in the phantom of FIG. 2, the geometric relationships among the various targets is known a priori, and thus multiple comparisons can be made among expected doses for the two treatments plans, as applied to either target, or the measured dosages themselves, to either refine the performance metric or to generate an additional performance metric. For example, expected doses could be calculated for the application of the second radiotherapy treatment plan to the first or second targets or the application of the first radiotherapy treatment plan to either of the first or second targets, and corresponding dosage measurements can be made and compared to these expected doses or to one another as part the evaluation of the radiotherapy system.

Where multiple metrics are used, each metric can represent a performance of a different stage or set of stages of an adaptive radiotherapy system. For example, a comparison of the expected dosage for the first plan as applied to the first target to the expected dosage for the second plan as applied to the second target can be used to evaluate the plan reoptimization stage of the adaptive radiotherapy system. Similarly, comparing the measured dosage for the first plan as applied to the second target to the measured dosage for the second plan as applied to the second target can be used to evaluate the overall effectiveness of the adaptive radiotherapy system in improving the outcome given the change in anatomy represented by the second target. Accordingly, the performance of the adaptive radiotherapy system can be evaluated both overall as well as at the level of the individual subsystems.

What have been described above are examples of the invention. It is, of course, not possible to describe every conceivable combination of components or methodologies, but one of ordinary skill in the art will recognize that many further combinations and permutations of the invention are possible. Accordingly, the invention is intended to embrace all such alterations, modifications and variations that fall within the scope of the appended claims and the application. Additionally, where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, the term "including" means including but not limited to. The term "based on" means based at least in part on.

What is claimed is:

1. An assembly comprising:
    a housing comprising a plurality of slots and formed from a first material having a first appearance under a selected imaging modality; and
    a plurality of inserts, each configured to be received by one of the plurality of slots, a given insert of the plurality of inserts comprising a target, formed from a second material having a second appearance under the selected imaging modality, such that the target is readily distinguishable from the housing under the selected imaging modality, the target associated with the given insert of the plurality of inserts comprising a hollow portion that can be accessed via a removable plug.

2. A system comprising:
    the assembly of claim 1, wherein the housing is a first housing, the plurality of slots is a first plurality of slots, and the plurality of inserts is a first plurality of inserts; and
    a second assembly positioned such that a surface of the second assembly overlaps a surface of the first assembly, the second assembly comprising:
        a second housing comprising a second plurality of slots and formed from the first material;
        a second plurality of inserts, each configured to be received by one of the second plurality of slots, each of the second plurality of inserts comprising a target formed from the second material.

3. The system of claim 2, further comprising a radiochromic film positioned between the surface of the second assembly and the surface of the first assembly.

4. The assembly of claim 1, wherein a first target, associated with a first insert of the plurality of inserts, has a known geometric relationship to a second target, associated with a second insert of the plurality of inserts, the known geometric relationship comprising a geometric transformation required to convert the morphology of the first target to the morphology of the second target.

5. The assembly of claim 4, wherein the first target represents the second target with an asymmetric deformation.

6. The assembly of claim 4, wherein the first target represents the second target with a known rotation.

7. The assembly of claim 4, wherein the first target represents the second target with a known translation.

8. The assembly of claim 4, wherein the first target represents the second target with a known reduction in volume.

9. The assembly of claim 1, wherein the removable plug is a first removable plug and the hollow portion of the target that can be accessed via the first removable plug, on a first surface of the target, and a second removable plug, on a second surface of the target.

10. A system comprising:
the assembly of claim 1, wherein the housing is a first housing, the plurality of slots is a first plurality of slots, and the plurality of inserts is a first plurality of inserts, with the first plurality of inserts comprising a respective first plurality of targets, such that each of the first plurality of inserts comprises an associated one of the first plurality of targets; and
a second assembly comprising:
a second housing comprising a second plurality of slots and formed from the first material;
a second plurality of inserts, each configured to be received by one of the second plurality of slots, the second plurality of inserts comprising a respective second plurality of targets formed from the second material, such that each of the second plurality of inserts comprises an associated one of the second plurality of targets;
wherein the second housing is aligned with first housing such that the removable plug of each of the first plurality of targets is aligned with a corresponding removable plug of an associated one of the second plurality of targets.

11. The system of claim 10, further comprising a dosimeter positioned to extend between the hollow portion of the target associated with the given one of the first plurality of inserts and the hollow portion of the target associated with a corresponding insert of the second plurality of inserts.

12. An assembly comprising:
a housing comprising a plurality of slots and formed from a first material having a first appearance under a selected imaging modality; and
a plurality of inserts, each configured to be received by one of the plurality of slots, each insert comprising a frame, formed from one of the first material and a second material having the first appearance under the selected imaging modality, and a target, formed from a third material having a second appearance under the selected imaging modality, such that the target is readily distinguishable from the housing and the frame under the selected imaging modality, a first target of the plurality of targets having a known geometric relationship to a second target of the plurality of targets and a hollow portion that can be accessed via a removable plug.

* * * * *